US012729396B2

(12) United States Patent
Ross et al.

(10) Patent No.: US 12,729,396 B2
(45) Date of Patent: Sep. 8, 2026

(54) METHOD FOR QUANTITATIVE MONITORING mRNA CAPPING EFFICIENCY

(71) Applicant: THERMO FINNIGAN LLC, San Jose, CA (US)

(72) Inventors: Robert L. Ross, Hopkinton, MA (US); Min Du, Acton, MA (US)

(73) Assignee: Thermo Finnigan LLC, San Jose, CA (US)

( * ) Notice: Subject to any disclaimer, the term of this patent is extended or adjusted under 35 U.S.C. 154(b) by 381 days.

(21) Appl. No.: 18/558,268

(22) PCT Filed: Mar. 16, 2023

(86) PCT No.: PCT/US2023/064530
§ 371 (c)(1),
(2) Date: Oct. 31, 2023

(87) PCT Pub. No.: WO2023/201161
PCT Pub. Date: Oct. 19, 2023

(65) Prior Publication Data

US 2024/0240236 A1 Jul. 18, 2024

Related U.S. Application Data

(60) Provisional application No. 63/331,407, filed on Apr. 15, 2022.

(51) Int. Cl.
*C12Q 1/6809* (2018.01)
*C12Q 1/48* (2006.01)
*C12Q 1/6806* (2018.01)

(52) U.S. Cl.
CPC ............ *C12Q 1/6809* (2013.01); *C12Q 1/48* (2013.01); *C12Q 1/6806* (2013.01); *G01N 2333/91011* (2013.01)

(58) Field of Classification Search
None
See application file for complete search history.

(56) References Cited

U.S. PATENT DOCUMENTS 3,755,086 A * 8/1973 Heimer .................... C12Q 1/48 435/6.1
10,612,088 B2 * 4/2020 Shishkin .............. C12Q 1/6874
2020/0399677 A1 * 12/2020 MacDonald ........... C12Q 1/682

FOREIGN PATENT DOCUMENTS

CN 107460219 A 12/2017

OTHER PUBLICATIONS

Reichle et al. Methods 156. pp. 91-101 (Year: 2019).*
Muthmann et al. "Quanitification of mRNA cap-modifications by means of LC-QqQ-MS" Methods, 2022, vol. 203. pp. 196-206.

* cited by examiner

*Primary Examiner* — Blaine Lankford

(57) ABSTRACT

A method for quantifying mRNA capping efficiency includes combining a sample, an enzyme mixture, and an isotopic standard solution in a buffer solution to create an incubation mixture, the enzyme mixture including a non-specific, single-stranded nuclease and an acid phosphatase and the isotopic standard including isotopically labeled m7G and isotopically labeled 2'-O-methylated nucleoside; incubating the mixture; and analyzing the mixture using liquid chromatography-mass spectrometry to determine at least one of a capping efficiency and a 2-O-methyltransferase efficiency.

24 Claims, 5 Drawing Sheets

7-methylguanosine

FIG. 1A

2'-O-methyladenosine

FIG. 1B

Cap(0) Structure

FIG. 2A

Cap(1) Structure m7G(D)

Am(D)

METHOD FOR QUANTITATIVE MONITORING mRNA CAPPING EFFICIENCY

RELATED APPLICATIONS

This application is a national stage filing under 35 U.S.C. § 371 of PCT International application PCT/US2023/064560 filed Mar. 16, 2023, which claims priority to provisional patent application U.S. 63/331,407, filed on Apr. 15, 2022. Each application named in this section is incorporated by reference herein, each in its entirety.

FIELD

The present disclosure generally relates to the field of mass spectrometry including a method for quantitative monitoring of mRNA capping efficiency.

INTRODUCTION

In Eukaryotic systems, non-mitochondrial messenger RNA (mRNA) are capped at the 5' end by an inverted 7-methylguanosine (m7G) (FIG. 1A) joined to the transcript by a 5' to 5' triphosphate linkage, m7G(5')ppp(5')N, referred to as Cap(0) (FIG. 2A). Once added to the transcript the first nucleotide in the strand (N), is then methylated at the 2' hydroxyl position to give the Cap(1) structure, m7G(5')ppp(5')Nm (FIG. 2B). For example, FIG. 1B shows 2'-O-methyladenosine. Alternately, Nm can be 2'-O-methylguanosine (Gm), 2'-O-methylcytosine Cm, or 2'-O-methyluridine (Um). Capping, as well as polyadenylation, help the transcript to resist degradation by the innate exonucleases in the cell. Besides blocking 5' to 3' exonucleases, the 5' cap facilitates exportation from the nucleus to the cytoplasm and aids the translation initiation process by acting as a determinate for ribosomal docking complexes.

Further alteration of the transcript called splicing events also rely on the cap structure. Parts of the transcript termed intragenic regions, or introns, are removed and the cleaved sections rejoined, leaving the coding region to be expressed (exon). The coding region is flanked on both sides, 5' and 3', by an untranslated region, a stretch of RNA which is not translated into protein but does influence translation. A matured mRNA transcript then consists of 5 sections, the 5' cap, the 5' UTR, the coding region, the 3' UTR and finally the polyadenylated tail (see FIG. 3).

Due to recent events, particularly the COVID pandemic, mRNA has been widely adopted as a useful therapy, such as various mRNA based COVID vaccines. Production of non-natural transcripts by in vitro transcription, may require the addition of the modified cap structure post purification to achieve the desired therapeutic function. Modified 5' caps can include an anti-reverse cap analogs (ARCA) (U.S. Pat. No. 7,074,596), TriLink Biotechnology's CleanCap analogs, or by a vaccinia capping enzyme followed by a methyltransferase reaction. Production of transcripts do necessitate analytical examination to determine reaction outcome and yield, however due to the size of the transcripts a direct measurement, such as with mass spectrometry, is technologically challenging. As such, improved techniques for measuring the capping and methylation efficiency are desirable.

SUMMARY

In a first aspect, a kit for quantifying mRNA capping efficiency can include an enzyme mixture including a Nuclease P1 and Sweet Potato Acid Phosphatase; and a standard mixture including isotopically labeled m7G and isotopically labeled 2'-O-methylated nucleoside. In various embodiments, the 2'-O-methylated nucleoside can be Am, Gm, Um, or Cm.

In various embodiments of the first aspect, the kit can further a buffer solution. In particular embodiments, the buffer solution can include $ZnCl_2$, such as at a $ZnCl_2$ concentration of between about 0.01 mmol and about 90 mmol. In particular embodiments, the buffer solution has a concentration of divalent cations of less than 100 mmol. In particular embodiments, the buffer solution can have a pH of between about 2 to about 7, such as between about 4 to about 6.

In various embodiments of the first aspect, the enzyme mixture can further include RNase T1.

In various embodiments of the first aspect, the enzyme mixture can be a lyophilized powder.

In various embodiments of the first aspect, the standards mixture can be a lyophilized powder.

In various embodiments of the first aspect, the isotopically labeled m7G and the isotopically labeled 2'-O-methylated nucleoside includes deuterium labeled m7G(D) and deuterium labeled 2'-O-methylated nucleoside.

In various embodiments of the first aspect, the isotopically labeled m7G and the isotopically labeled 2'-O-methylated nucleoside are $N^{15}$ labeled or $C^{13}$ labeled.

In various embodiments of the first aspect, the isotopically labeled m7G and the isotopically labeled 2'-O-methylated nucleoside in the standards mixture can be in a molar ratio of between about 2:1 to about 1:2. In particular embodiments, the standards mixture can include equimolar amounts of isotopically labeled m7G and isotopically labeled 2'-O-methylated nucleoside.

In a second aspect, a kit for quantifying mRNA capping efficiency can include an enzyme mixture including a non-specific, single-stranded nuclease and an acid phosphatase; a standard mixture including isotopically labeled m7G and isotopically labeled 2'-O-methylated nucleoside; and a buffer solution.

In various embodiments of the second aspect, the non-specific, single-stranded nuclease can include Nuclease P1.

In various embodiments of the second aspect, the acid phosphatase cannot be inhibited by adenosine monophosphate.

In various embodiments of the second aspect, the acid phosphatase can include Sweet Potato Acid Phosphatase.

In various embodiments of the second aspect, the enzyme mixture can include a site-specific, single-stranded RNA endonuclease.

In various embodiments of the second aspect, the site-specific, single-stranded RNA endonuclease can cleave RNA 3' of a guanosine.

In various embodiments of the second aspect, the site-specific, single-stranded RNA endonuclease can include Ribonuclease T1.

In various embodiments of the second aspect, the enzyme mixture can be a lyophilized powder.

In various embodiments of the second aspect, the standards mixture can be a lyophilized powder.

In various embodiments of the first aspect, the isotopically labeled m7G and the isotopically labeled 2'-O-methylated nucleoside include deuterium labeled m7G(D) and deuterium labeled 2'-O-methylated nucleoside.

In various embodiments of the first aspect, the isotopically labeled m7G and the isotopically labeled 2'-O-methylated nucleoside are $N^{15}$ labeled or $C^{13}$ labeled.

In various embodiments of the second aspect, the isotopically labeled m7G and isotopically labeled 2'-O-methylated nucleoside in the standards mixture can be in a molar ratio of between about 2:1 to about 1:2. In particular embodiments, the standards mixture can include equimolar amounts of isotopically labeled m7G and isotopically labeled 2'-O-methylated nucleoside.

In various embodiments of the second aspect, the buffer can include $ZnCl_2$ in a concentration range of about 0.001 mM and about 90 mM, such as between about 0.05 mM and about 0.2 mM. In particular embodiments, the buffer can include less than 100 mM of divalent cations.

In various embodiments of the second aspect, the buffer has a pH of between about 2 to about 7, such as between about 4 to about 6.

In a third aspect, a method for quantifying mRNA capping efficiency can include combining a sample, an enzyme mixture, and an isotopic standard solution in a buffer solution to create an incubation mixture, the enzyme mixture including a non-specific, single-stranded nuclease and an acid phosphatase and the isotopic standard including isotopically labeled m7G and isotopically labeled 2'-O-methylated nucleoside; incubating the mixture; analyzing the mixture using liquid chromatography-mass spectrometry to determine at least one of a capping efficiency and a 2'-O-methyltransferase efficiency.

In various embodiments of the third aspect, incubating the mixture can be performed at a temperature of between about 30° C. and 70° C., such as between about 35° C. and 45° C.

In various embodiments of the third aspect, non-specific, single-stranded nuclease can include Nuclease P1.

In various embodiments of the third aspect, acid phosphatase cannot be inhibited by adenosine monophosphate.

In various embodiments of the third aspect, the acid phosphatase can include Sweet Potato Acid Phosphatase.

In various embodiments of the third aspect, the enzyme mixture can further include a site-specific, single-stranded RNA endonuclease. In particular embodiments, the site-specific, single-stranded RNA endonuclease can cleave RNA 3' of a guanosine.

In particular embodiments, the site-specific, single-stranded RNA endonuclease can include Ribonuclease T1. In further embodiments, incubating the mixture can be performed at a temperature of between about 30° C. and 50° C.

In various embodiments of the third aspect, the incubation mixture can include between about 0.5 units and about 10.0 units of the site-specific, single-stranded RNA endonuclease, such as between about 0.5 and about 2.0 units.

In various embodiments of the third aspect, the method can further include solubilizing a lyophilized enzyme mixture with the sample buffer to obtain the enzyme mixture.

In various embodiments of the third aspect, the method can further include solubilizing a lyophilized standards mixture with the sample buffer to obtain the standards mixture.

In various embodiments of the third aspect, the incubation mixture can include between about 0.5 units and about 10.0 units of the acid phosphatase, such as between about 0.5 units and about 2.0 units.

In various embodiments of the third aspect, the incubation mixture can include between about 1 unit and 100 units of the non-specific, single-stranded nuclease, such as between about 5 units and about 20 units.

In various embodiments of the third aspect, the isotopically labeled m7G and the isotopically labeled 2'-O-methylated nucleoside includes deuterium labeled m7G(D) and deuterium labeled 2'-O-methylated nucleoside In various embodiments of the third aspect, the isotopically labeled m7G and the isotopically labeled 2'-O-methylated nucleoside are $N^{15}$ labeled or $C^{13}$ labeled.

In various embodiments of the third aspect, the isotopically labeled m7G and the isotopically labeled 2'-O-methylated nucleoside in the standards mixture are in a molar ratio of between about 2:1 to about 1:2, such as in equimolar amounts of isotopically labeled m7G and isotopically labeled 2'-O-methylated nucleoside.

In various embodiments of the third aspect, the incubation mixture can include an amount of isotopically labeled m7G of between about 1.0 nmol and 20 nmol. In particular embodiments, the incubation mixture can include an amount of isotopically labeled 2'-O-methylated nucleoside of between about 1.0 nmol and about 20 nmol.

In various embodiments of the third aspect, the buffer can include $ZnCl_2$ in a concentration range of about 0.001 mM and about 90 mM. In particular embodiments, the buffer can include $ZnCl_2$ in a concentration range of about 0.05 mM and about 0.2 mM.

In various embodiments of the third aspect, the incubation mixture can include less than 100 mM of divalent cations.

In various embodiments of the third aspect, the buffer can have a pH of between about 2 to about 7, such as between about 4 to about 6.

In various embodiments of the third aspect, analyzing the mixture using liquid chromatography-mass spectrometry further includes separating the mixture using a chromatography column, obtaining m/z and intensity data using the mass spectrometer, identifying and integrating the peaks for m7G and isotopically labeled m7G, peaks for 2'-O-methylated nucleoside and isotopically labeled 2'-O-methylated nucleoside, or both; calculating a m7G:isotopically labeled m7G peak ratio, a 2'-O-methylated nucleoside:isotopically labeled 2'-O-methylated nucleoside peak ratio, or both; and determining the capping efficiency based on the m7G:isotopically labeled m7G peak ratio, the 2'-O-methyltransferase efficiency based on the 2'-O-methylated nucleoside:isotopically labeled 2'-O-methylated nucleoside peak ratio or both.

DRAWINGS

For a more complete understanding of the principles disclosed herein, and the advantages thereof, reference is now made to the following descriptions taken in conjunction with the accompanying drawings, in which:

Figures 1A, 1B, 2A:
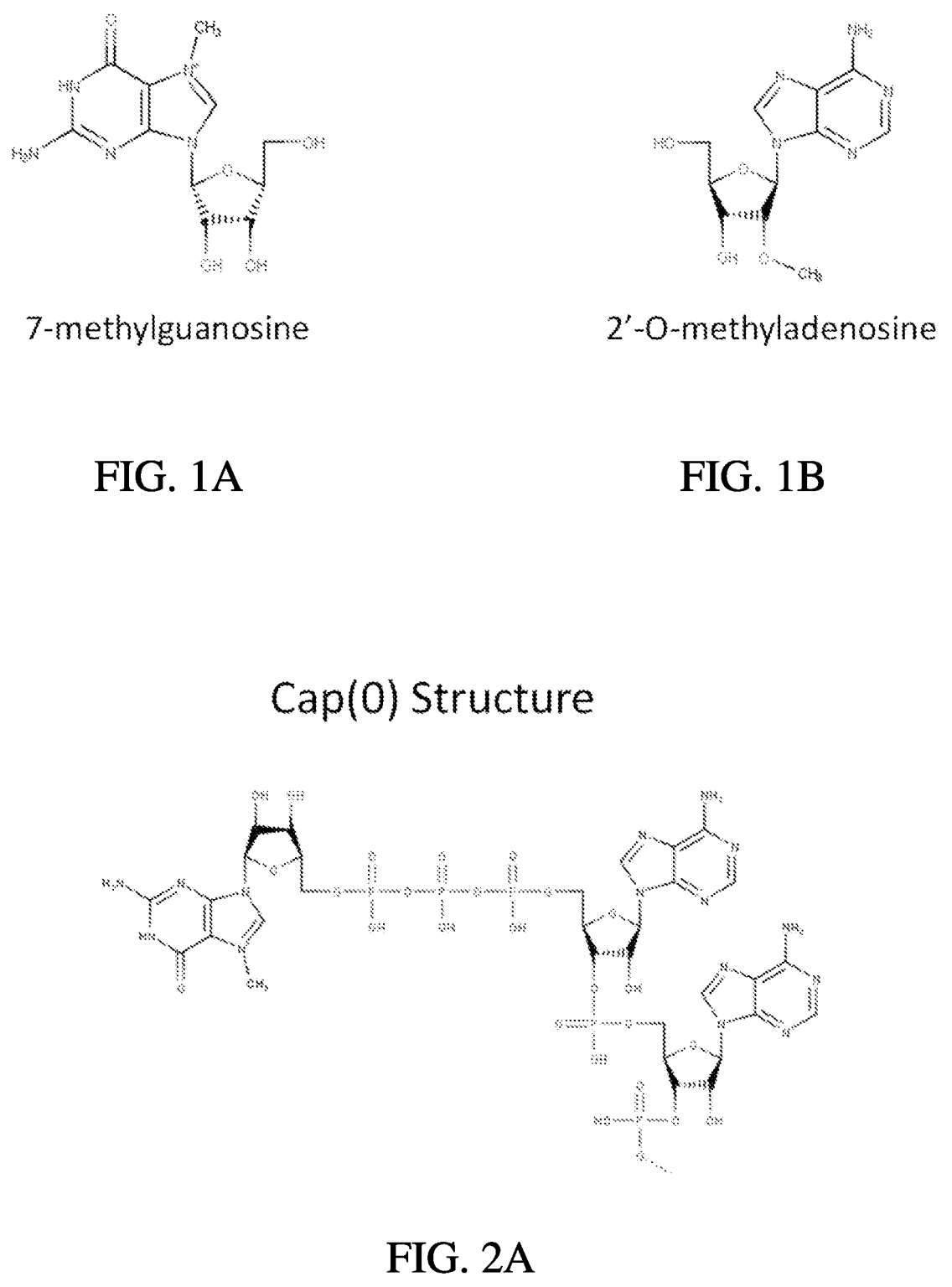

FIGS. 1A and 1B are diagrams illustrating the chemical structure of 7-methylguanosine and 2'-O-methyladenosine respectively.

FIGS. 2A and 2B are diagrams illustrating the chemical structure of Cap(0) and Cap(1) respectively.

FIG. 3 is a diagram illustrating the structure of mRNA.

Figures 2B, 3:
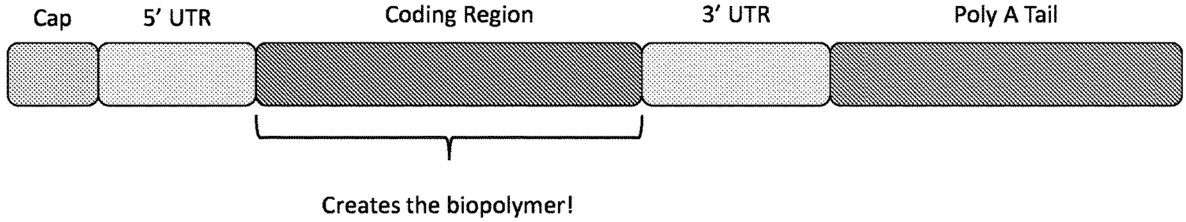

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of ion mobility enhanced qualitative and quantitative methods are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Production of transcripts can necessitate analytical examination to determine reaction outcome and yield. However, due to the size of the transcripts. a direct measurement, such as with mass spectrometry, is technically challenging. Two published analytical methods using enzymes to digest the transcripts into a more manageable size range have been developed. The first, named CapMap, uses the digestive enzyme nuclease P1 to reduce the intact transcript down to its individual 5' phosphorylated nucleotides and reported to also produce the cap dinucleotide. The digestion mixture is then spiked with an ARCA dinucleotide, separated on a porous graphitic carbon packed chromatography column, and analyzed by mass spectrometry. Two challenges are observed with this method, the first being control of the digestion enzyme, with the second being the chromatography platform. It is well known that the enzyme nuclease P1, which the authors use as the sole digestive system, results in the production of 5' monophosphates. All cap structures are joined 5' to 5', which when subjected to nuclease P1, results in cleavage of the m7G nucleotide as well as the first nucleotide in the strand, usually the 2'-O-methyladenosine, although other 2'-O-mythelated nucleosides are possible. Secondly porous graphitic carbon packed chromatography columns are known to degrade over injections and needs to be reconditioned. Taken together, the CAPMAP approach could yield an incorrect measurement, either by partial digestion or poor chromatographic peak integration.

The second method uses the digestive enzyme RNase H. RNase H will cleave the RNA strand in an RNA:DNA double stranded hybrid at the Watson-Crick RNA:DNA base pair. The method, published by Beverly (Beverly, M.; Dell, A.; Parmar, P.; Houghton, L. Label-Free Analysis of MRNA Capping Efficiency Using RNase H Probes and LC-MS. Anal. Bioanal. Chem. 2016, 408 (18), 5021-5030) involves designing a biotinylated molecular probe ~25 nt in length, complementary to the 5' end of the transcript. The probe is annealed to the 5' end of the mRNA, followed by complexing to magnetic beads, then subjected to an RNase H digestion. The cleaved products are separated by a magnet, washed, eluted from bead and probe with hot methanol water, dried, then analyzed by LC-MS. The results will show that capping has occurred. However, the authors of the method note that their recovery rate was less than 60%. Furthermore, published data on RNase H1, the commercially available enzyme referenced in the Beverly paper, will not cleave at a single RNA:DNA base pair, but will instead produce multiple cleavage products down strand from the chimeric base pairing. When replicating the digestion, it is possible to detect multiple different oligonucleotides, with 3' cleaved ends 1 to 2 nucleotides down strand from the RNA:DNA base pair. Furthermore, due to sequence homology between different nucleotide sections of the 5' end of the mRNA, off target RNase H cleavage products can also detected at high abundance.

Method for Determining Capping and Methylation Efficiency

Figures 4A, 4B, 5:
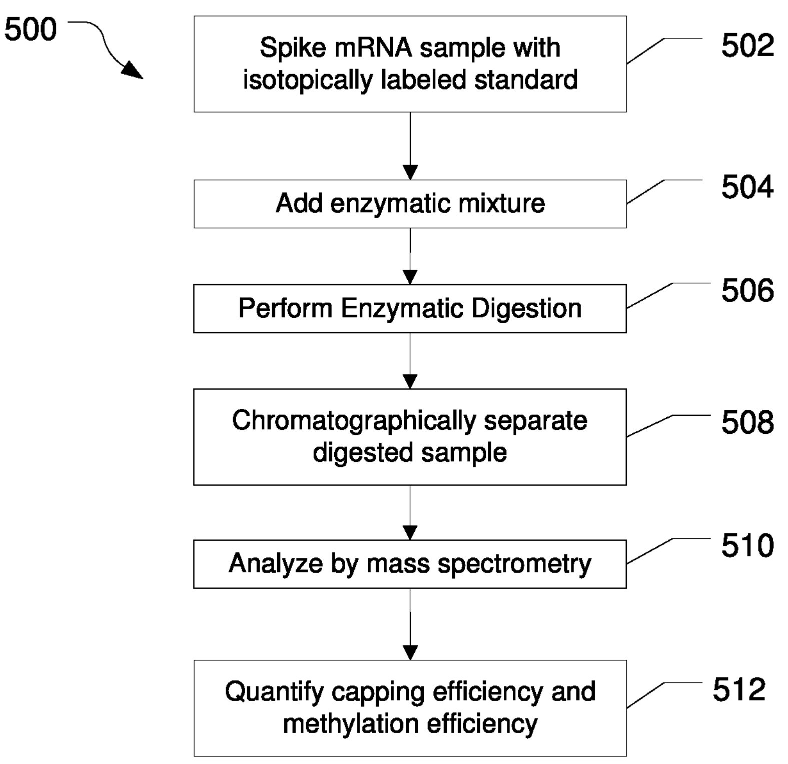
FIGS. 4A and 4B are diagrams illustrating the chemical structure of deuterated 7-methylguanosine and deuterated 2'-O-methyladenosine respectively, in accordance with various embodiments.
FIG. 5 is a flow diagram a method of determining the capping efficacy and 2'-O-methyltransferase efficiency, in accordance with various embodiments.

Described herein is a method for direct measurement of both 5' capping as well as 2'-O-methyltransferase efficiency. An aliquot of mRNA can be spiked with a known amount of isotopically labeled $m^7G$ and an isotopically labeled 2'-O-methylated nucleoside, such as 2'-O-methyladenosine (Am), 2'-O-methylguanosine (Gm), 2'-O-methylcytosine Cm, or 2'-O-methyluridine (Um). FIG. 4A shows isotopically labeled $m^7G$ labeled with 3 deuterium atoms at the methyl group $m^7G(D)$. Similarly, FIG. 4B shows isotopically labeled Am labeled with 3 deuterium atoms at the methyl group Am(D). A single enzymatic digestion can then be performed to reduce the mRNA to its individual nucleosides. The spiked digest can then be separated chromatographically using a simple ammonium-based buffer system and analyzed by mass spectrometry. Accurate quantification can be performed by comparing peak areas of heavy vs light m7G/2'O-methylated nucleoside.

In other embodiments, the isotopically labeled standard can include isotopically labeled 5' phosphate-$m^7G$ and an isotopically labeled 5'-phosphate-2'-O-methylated nucleotide. In this scenario, the phosphatase can cleave the 5' phosphate from the isotopically labeled standards resulting in the isotopically labeled methylated nucleosides.

Mass spectrometry has proven to be a robust and reliable application for the direct measurement of biomolecules. By transitioning a biomolecule from a liquid or solid substrate into the gas phase as an ion, the mass of the ion can be detected and measured. One method for producing the ion is electrospray ionization (ESI). Quantification of molecules produced by ESI can be performed using a standard curve, where known amounts of a synthetic standard are acquired and the results plotted, the equation of the slope can be used to find the concentration of the target in a sample. Challenges posed by generation of a standard curve are predominately finding/generating a synthetic standard and matching the matrix of the target sample. Matrix matching is important due to the nature of ESI, where every polar molecule in a sample competes for surface charge. This competition for charge can cause the measured response in the sample to vary from that of the standard curve, causing error in measurement. A more accurate measurement of a molecule is performed by spiking the sample with an isotopically labeled standard. In this method, a synthetic standard of the target molecule is created, where one or more of the atoms are replaced with its stable isotope, $C^{13}$ for carbon, $N^{15}$ for nitrogen and Deuterium (D) for hydrogen. A known amount of the stable isotope labeled standard (SILS) is spiked into the sample and the sample is processed and acquired. Since the SILS is structurally identical to the target molecule, it will have identical elution profile as the molecule under investigation, the only difference being a shift in mass. The spiked SILS will undergo the same ionization charge competition as the target molecule, avoiding any measurement errors that may have arisen when trying to match matrices. By taking the ratio of the heavy to light peak areas, the amount of target molecule is quantified. For RNA nucleoside analysis the main hinderance to this approach was the availability of SILS. The approach described herein uses only the purified heavy labeled nucleoside molecule as an internal standard, without the need for cell culture, RNA purification, and dilution of the sample, and results in a precise measurement of the target molecule.

FIG. 5 illustrates method 500 of measuring 5' capping efficiency and/or 2'-O-methyltransferase efficiency. At 502, the mRNA sample can be spiked with isotopically labeled standards, such as isotopically labeled m7G and isotopically labeled 2'-O-methylated nucleoside. In various embodiments, the isotopically labeled m7G and 2'-O-methylated nucleoside can be deuterium labeled, such as m7G(D) and Am(D), or can be labeled with $N^{15}$ or $C^{13}$. In various embodiments, the isotopically labeled m7G and the isotopically labeled 2'-O-methylated nucleoside can be in a molar ratio of between about 2:1 to about 1:2, such as in equimolar amounts. The concentration of the standard can be such that the amount of isotopically labeled m7G in an incubation mixture can be between about 1.0 nmol and 20 nmol and the amount of isotopically labeled 2'-O-methylated nucleoside in the incubation mixture of between about 1.0 nmol and about 20 nmol.

At 504, an enzyme mixture can be added to the sample. The enzyme mixture can include a non-specific, single-stranded nuclease, such as Nuclease P1, and an acid phosphatase, such as Sweet Potato Acid Phosphatase. A significant feature of the acid phosphatase can be that it is not inhibited by adenosine monophosphate, as digestion of the mRNA to monophosphates by Nuclease P1 would result in production of adenosine monophosphate that may inhibit some acid phosphatases. Optionally, the enzyme mixture can include a site-specific, single-stranded RNA endonuclease, such as an endonuclease that cleaves RNA 3' of a guanosine. Examples of site-specific, single-stranded RNA endonuclease that cleave RNA 3' of a guanosine include RNase T1, RNase N1, RNase Sa, Barnase, and other similar endonuclease.

In various embodiments, the enzyme mixture can include sufficient non-specific, single-stranded nuclease such that between about 1 units and about 100 units of the non-specific, single-stranded nuclease is added to the mRNA sample, such as between about 5 units and about 20 units. In various embodiments, the enzyme mixture can include sufficient acid phosphatase such that between about 0.5 units and about 10.0 units of the acid phosphatase is added to the mRNA sample, such as between about 0.5 units and about 2.0 units. In various embodiments, the enzyme mixture can include sufficient site-specific, single-stranded RNA endonuclease (when present) such that between about 0.5 units and about 10.0 units of the site-specific, single-stranded RNA endonuclease is added to the mRNA sample, such as between about 0.5 units and about 2.0 units. It is know that increasing the amount of enzyme can shorten the time to completion and one of skill in the art can identify a suitable amount of enzyme for a desired incubation period.

In various embodiments, the mRNA sample, the isotopically labeled standard, and/or the enzyme mixture can be dry and reconstituted by adding a buffer solution. For example, the mRNA sample can be precipitated and the supernatant can be removed, such as to remove salts and solvents from the synthesis of the mRNA that can interfere with the enzymatic digestion. In a further example, the isotopically labeled standard and the enzyme mixture can be provided as a lyophilized powder, such as to extend shelf life Alternatively, the standard or enzyme mixture can be frozen solutions that are thawed as needed. In various embodiments, the precipitated mRNA can be reconstituted with a specified amount of buffer and the enzyme mixture and isotopically labeled standards can be added in specific amounts. Alternatively, specific amounts of the enzyme mixture and isotopically labeled standards can be added to the precipitated mRNA and the mRNA can be reconstituted such as by mixing.

In various embodiments, the buffer can include $ZnCl_2$ in a concentration range of about 0.001 mM and about 90 mM, such as in a concentration range of about 0.05 mM and about 0.2 mM. Further, the incubation mixture includes less than 100 mM of divalent cations. In various embodiments, the buffer can have a pH of between about 2 to about 7, such as a pH of between about 4 to about 6.

At 506, an enzymatic digestion of the mRNA can be performed. In various embodiments, the incubation mixture including the mRNA, the isotopically labeled standards, and the enzyme mixture can be incubated at a temperature of between about 30° C. and about 70° C., such as between about 30° C. and about 50° C., even between about 35° C. and about 45° C. The enzymatic digestion can be carried out for sufficient time for the nuclease(s) to digest the mRNA to component nucleotides and for the acid phosphatase to convert the nucleotides to nucleosides by remove the phosphates from the nucleotides. In various embodiments, the enzymatic digestion can be carrier out for at least about 30 minutes, such as at least about 45 minutes, such as at least about 1 hour, such as at least about 4 hours, such as at least about overnight (~12-16 hours). Generally, the enzymatic digestion can be less than about a day.

At 508, the digested sample can be chromatographically separated, and, at 510, the chromatographically separated sample can be analyzed by mass spectrometry. This can include obtaining m/z and intensity data using the mass spectrometer, identifying and integrating the peaks for m7G and isotopically labeled m7G and/or the peaks for 2'-O-methylated nucleoside and isotopically labeled 2'-O-methylated nucleoside. Further, at 512, the capping efficiency can be determined from the m7G:isotopically labeled m7G peak ratio and the 2-O-methyltransferase efficiency can be determined based on the 2'-O-methylated nucleoside:isotopically labeled 2'-O-methylated nucleoside peak ratio.

Enzymatic Digestion Kit

In various embodiments, a kit for quantifying mRNA capping efficiency can include an enzyme mixture and an isotopically labeled standards mixture. The enzyme mixture and the isotopically labeled standards mixture can be lyophilized powders that can be reconstituted with the addition of a buffer. In other embodiments, enzyme mixture and the isotopically labeled standards mixture can be solutions, such as frozen solutions. It can be advantageous for the enzyme mixture and the isotopically labeled standards mixture can be in small quantities, such as single use tubes sufficient for one or a few reactions rather than bulk solutions that can be used for dozens of reactions.

The enzyme mixture can include a non-specific, single-stranded nuclease and an acid phosphatase. The non-specific, single-stranded nuclease can include a Nuclease P1. The acid phosphatase can be an acid phosphatase that is not inhibited by adenosine monophosphate, such as Sweet Potato Acid Phosphatase. The enzyme mixture can include a site-specific, single-stranded RNA endonuclease, such as a site-specific, single-stranded RNA endonuclease that cleaves RNA 3' of a guanosine. In various embodiments, the site-specific, single-stranded RNA endonuclease can include RNase T1, RNase N1, RNase Sa, Barnase, and other similar endonuclease.

The isotopically labeled standards mixture can include isotopically labeled m7G and 2'-O-methylated nucleoside. Generally, the isotopically labeled standards mixture can include heavy stable isotopes incorporated into the compounds of the standard. The use of heavy stable isotopes can shift the m/z charge ratio without altering the chemical properties of the compounds allowing for their use as internal standards in mass spectroscopy. In various embodiments, the isotopically labeled standard mixture can include isotopically labeled m7G and 2'-O-methylated nucleoside. The isotopically labeled m7G and the 2'-O-methylated nucleoside can be deuterium labeled, $N^{15}$ labeled, $C^{11}$ labeled, $O^{17}$ labeled, $O^{18}$ labeled, or any combination thereof. The isotopically labeled standards mixture can include isotopically labeled m7G and isotopically labeled 2'-O-methylated nucleoside in a molar ratio of between about 2:1 to about 1:2, such as equimolar amounts of isotopically labeled m7G and isotopically labeled 2'-O-methylated nucleoside.

In other embodiments, the isotopically labeled standards mixture can include isotopically labeled 5' phosphate-$m^7G$ and an isotopically labeled 5'-phosphate-2'-O-methylated nucleotide. In this scenario, the phosphatase can cleave the 5' phosphate from the isotopically labeled standards resulting in the isotopically labeled methylated nucleosides.

The kit may also include a buffer solution. The buffer solution can include $ZnCl_2$ such as in a concentration of between about 0.01 mmol and about 90 mmol. The buffer solution can have a concentration of divalent cations of less than 100 mmol. The buffer solution has a pH of between about 2 to about 7, such as between about 4 to about 6.

Chromatography Platform

Figure 6:
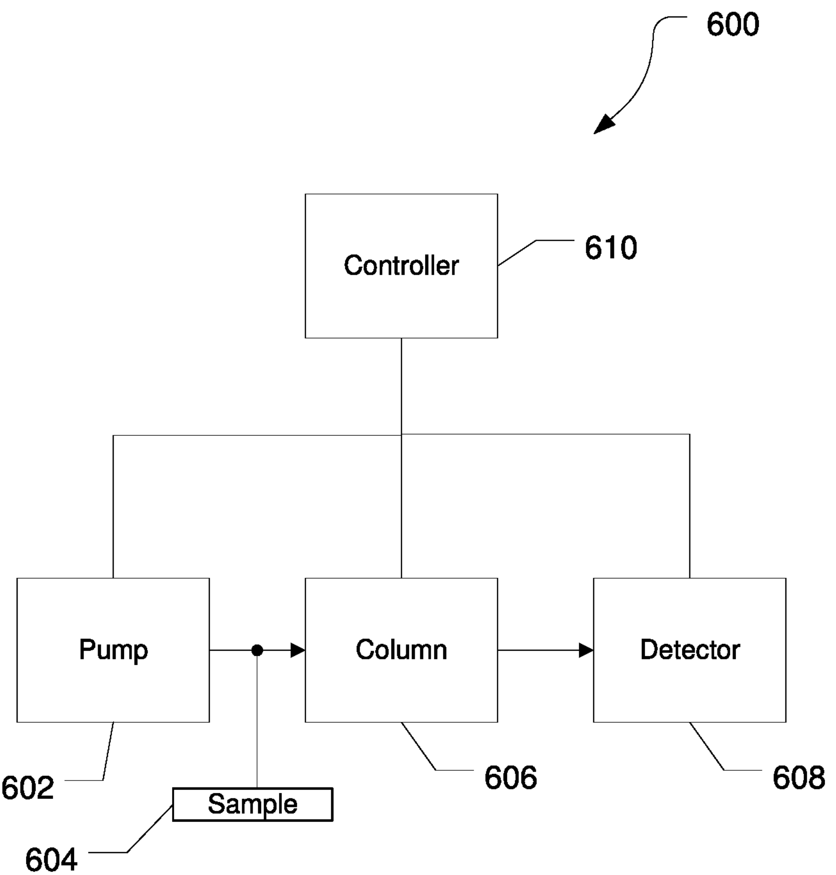
FIG. 6 is a block diagram of an exemplary chromatography system, in accordance with various embodiments.

FIG. 6 depicts a liquid chromatography system 600 according to one aspect of the invention. The liquid chromatography system 600 comprises an analytical pump 602 to pump a solvent through the system 600. The system 600 comprises a sample reservoir 604 comprising a sample to be analysed. The system 600 further comprises a separation column 606 and a detector 608. System 600 also comprises a controller 610.

The liquid chromatography system 600 is adapted to retrieve a sample from the sample reservoir 604. The sample can then be introduced into the system The liquid chromatography system 1000 is further adapted to introduce the sample into the separation column 606.

The system 600 is also adapted to inject the sample into the separation column 606 by means of the analytical flow. This can be done by guiding the sample by means of the analytical pump 602. The separation column 606 can separate the sample into component species based on retention time within the separation column 606. After separation of the sample by the separation column 606, the separated components can be detected by a detector 608. In some embodiments, the detector 608 can be an optical detector, such as an absorption detector, refractive index detector, a fluorescence detector, or the like. In other embodiments, the detector 608 can be a conductivity detector or an electrochemical detector. In yet other embodiments, the detector 608 can be a mass spectrometer.

In various embodiments, the separation column 606 generally consists of a tube packed with a stationary phase medium. The stationary phase medium can affect the time it takes for a compound to travel through the column (retention time). The effect can be different for different compounds, such that individual components of a sample can be separated based on their respective retention times. There are a variety of stationary phase mediums, including porous materials, ionic materials, polar materials, non-polar materials, and the like. Porous materials can affect retention time based on the size of a molecule and the ability of the molecule to enter the porous material. Ionic materials can affect retention time based on charge attraction or repulsion between the ionic material and the compounds. Polar and non-polar materials can affect retention time based on the hydrophobicity or hydrophilicity of the compounds.

In various embodiments, nucleotides and nucleosides can be separated using a reverse phase separation in which a hydrophobic non-polar stationary phase material is used along with mobile phase with varying hydrophobicity depending on the ratio of polar to organic solvents. For example, a C18 column can be used with an ammonium acetate or ammonium formate buffer system to separate the nucleosides. In particular embodiments, an aqueous mobile phase of 5 mM ammonium acetate at a pH of about 5 can be used and a gradient of increasing concentrations of acetonitrile (up to about 40%) or methanol (up to about 50%) can be used to separate the nucleosides. Suitable columns and buffer systems would be apparent to one of skill in the art and are within the scope of this disclosure.

In other embodiments, nucleotides and nucleosides can be separated using hydrophilic interaction liquid chromatography (HILIC) in which a hydrophilic stationary phase material is used along with hydrophobic mobile phase, such as acetonitrile. Suitable columns and buffer systems would be apparent to one of skill in the art and are within the scope of this disclosure.

Mass Spectrometry Platform

Figure 7:
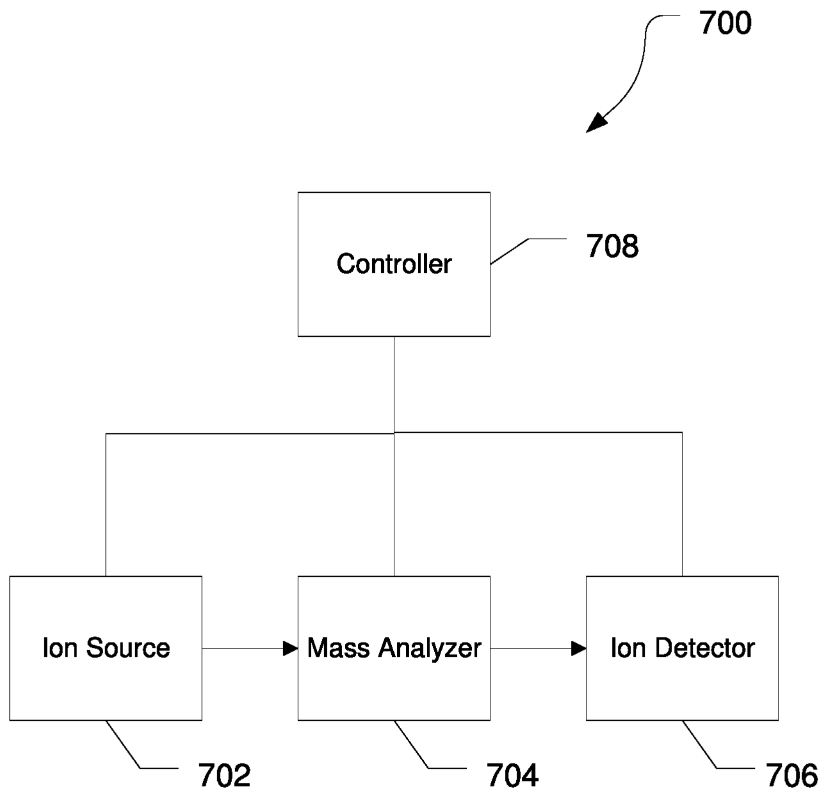
FIG. 7 is a block diagram of an exemplary mass spectrometry system, in accordance with various embodiments.

Various embodiments of mass spectrometry platform 700 can include components as displayed in the block diagram of FIG. 7. In various embodiments, mass spectrometry platform 700 can operate as a detector 608 of system 600. In various embodiments, elements of FIG. 7 can be incorporated into mass spectrometry platform 700. According to various embodiments, mass spectrometer 700 can include an ion source 702, a mass analyzer 704, an ion detector 706, and a controller 708.

In various embodiments, the ion source 702 generates a plurality of ions from a sample. The ion source can include, but is not limited to, a matrix assisted laser desorption/ionization (MALDI) source, electrospray ionization (ESI) source, atmospheric pressure chemical ionization (APCI) source, atmospheric pressure photoionization source (APPI), inductively coupled plasma (ICP) source, electron ionization source, chemical ionization source, photoionization source, glow discharge ionization source, thermospray ionization source, and the like.

In various embodiments, the mass analyzer 704 can separate ions based on a mass-to-charge ratio of the ions. For example, the mass analyzer 704 can include a quadrupole mass filter analyzer, a quadrupole ion trap analyzer, a time-of-flight (TOF) analyzer, an electrostatic trap (e.g., Orbitrap) mass analyzer, Fourier transform ion cyclotron resonance (FT-ICR) mass analyzer, and the like. In various embodiments, the mass analyzer 704 can also be configured to fragment the ions using collision induced dissociation (CID) electron transfer dissociation (ETD), electron capture dissociation (ECD), photo induced dissociation (PID), surface induced dissociation (SID), and the like, and further separate the fragmented ions based on the mass-to-charge ratio.

In various embodiments, the ion detector 706 can detect ions. For example, the ion detector 706 can include an electron multiplier, a Faraday cup, and the like. Ions leaving the mass analyzer can be detected by the ion detector. In various embodiments, the ion detector can be quantitative, such that an accurate count of the ions can be determined.

In various embodiments, the controller 708 can communicate with the ion source 702, the mass analyzer 704, and the ion detector 706. For example, the controller 708 can configure the ion source or enable/disable the ion source. Additionally, the controller 708 can configure the mass analyzer 704 to select a particular mass range to detect. Further, the controller 708 can adjust the sensitivity of the ion detector 706, such as by adjusting the gain. Additionally, the controller 708 can adjust the polarity of the ion detector 706 based on the polarity of the ions being detected. For example, the ion detector 706 can be configured to detect positive ions or be configured to detected negative ions.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A method for quantifying mRNA capping efficiency comprising:

combining an mRNA sample, an enzyme mixture, and an isotopic standard solution in a buffer solution to create an incubation mixture, the enzyme mixture including a non-specific, single-stranded nuclease and an acid phosphatase and the isotopic standard including isotopically labeled m7G and isotopically labeled 2'-0-methylated nucleoside (Am, Gm, Cm, or Um);

incubating the mixture; and analyzing the mixture using liquid chromatography-mass spectrometry to determine at least one of a capping efficiency and a 2'-0-methyltransferase efficiency.

2. The method of claim 1 incubating the mixture is performed at a temperature of between about 30° C. and 70° C.

3. The method of claim 2 incubating the mixture is performed at a temperature of between about 35° C. and 45° C.

4. The method of claim 1 wherein the non-specific, single-stranded nuclease includes Nuclease P1.

5. The method of claim 1 wherein the acid phosphatase is not inhibited by adenosine monophosphate.

6. The method of claim 1 wherein the acid phosphatase includes Sweet Potato Acid Phosphatase.

7. The method of claim 1 wherein the enzyme mixture further includes a site-specific, single-stranded RNA endonuclease.

8. The method of claim 7 wherein the site-specific, single-stranded RNA endonuclease cleaves RNA 3' of a guanosine.

9. The method of claim 7 wherein the site-specific, single-stranded RNA endonuclease includes Ribonuclease T1.

10. The method of claim 9 incubating the mixture is performed at a temperature of between about 30° C. and 50° C.

11. The method of claim 1 further comprising solubilizing a lyophilized enzyme mixture with the sample buffer to obtain the enzyme mixture.

12. The method of claim 1 further comprising solubilizing a lyophilized standards mixture with the sample buffer to obtain the standards mixture.

13. The method of claim 1, wherein the isotopically labeled m7G and the isotopically labeled 2'-O-methylated nucleoside includes deuterium labeled m7G(D) and deuterium labeled 2'-O-methylated nucleoside (Am(D), Gm(D), Cm(D), or Um(D)).

14. The method of claim 1, wherein the isotopically labeled m7G and the isotopically labeled 2'-O-methylated nucleoside are $N^{15}$ labeled or $C^{13}$ labeled.

15. The method of claim 1 wherein the isotopically labeled m7G and the isotopically labeled 2'-O-methylated nucleoside in the standards mixture are in a molar ratio of between about 2:1 to about 1:2.

16. The method of claim 15 wherein the standards mixture includes equimolar amounts of isotopically labeled m7G and isotopically labeled 2'-O-methylated nucleoside.

17. The method of claim 1 wherein incubation mixture includes an amount of isotopically labeled m7G of between about 1.0 nmol and 20 nmol.

18. The method of claim 17 wherein incubation mixture includes an amount of isotopically labeled 2'-O-methylated nucleoside of between about 1.0 nmol and about 20 nmol.

19. The method of claim 1 wherein the buffer includes $ZnCl_2$ in a concentration range of about 0.001 mM and about 90 mM.

20. The method of claim 19 wherein the buffer includes ZnCl2 in a concentration range of about 0.05 mM and about 0.2 mM.

21. The method of claim 1 wherein the incubation mixture includes less than 100 mM of divalent cations.

22. The method of claim 1 wherein the buffer has a pH of between about 2 to about 7.

23. The method of claim 22 wherein the buffer has a pH of between about 4 to about 6.

24. The method of claim 1 wherein analyzing the mixture using liquid chromatography-mass spectrometry further includes separating the mixture using a chromatography column, obtaining m/z and intensity data using the mass spectrometer, identifying and integrating the peaks for m7G and isotopically labeled m7G, peaks for 2'-O-methylated nucleoside and isotopically labeled 2'-O-methylated nucleoside, or both; calculating a m7G: isotopically labeled m7G peak ratio, a 2'-0-methylated nucleoside: isotopically labeled 2'-O-methylated nucleoside peak ratio, or both; and determining the capping efficiency based on the m7G: isotopically labeled m7G peak ratio, the 2-0-methyltransferase efficiency based on the 2'-O-methylated nucleoside: isotopically labeled 2'-O-methylated nucleoside peak ratio or both.

* * * * *